US010947598B2

United States Patent
Ricci et al.

(10) Patent No.: US 10,947,598 B2
(45) Date of Patent: Mar. 16, 2021

(54) METHODS FOR DETERMINING THE METABOLIC STATUS OF LYMPHOMAS (71) Applicants: INSERM (Institut National de la Sante et de la Recherche Medicale), Paris (FR); Universite Nice Sophia Antipolis, Nice (FR); Assistance Publique-Hopitaux de Paris (APHP), Paris (FR)

(72) Inventors: Jean-Ehrland Ricci, Nice (FR); Johanna Chiche, Nice (FR); Catherine Thieblemont, Paris (FR)

(73) Assignees: INSERM (INSTITUT NATIONAL DE LA SANTE ET DE LA RECHERCHE MEDICALE), Paris (FR); Université Côte d'Azur, Nice (FR); ASSISTANCE PUBLIQUE-HOPITAUX DE PARIS (APHP), Paris (FR)

(*) Notice: Subject to any disclaimer, the term of this patent is extended or adjusted under 35 U.S.C. 154(b) by 173 days.

(21) Appl. No.: 15/763,854

(22) PCT Filed: Sep. 29, 2016

(86) PCT No.: PCT/EP2016/073315
§ 371 (c)(1),
(2) Date: Mar. 28, 2018

(87) PCT Pub. No.: WO2017/055484
PCT Pub. Date: Apr. 6, 2017

(65) Prior Publication Data
US 2018/0282816 A1 Oct. 4, 2018

(30) Foreign Application Priority Data
Sep. 29, 2015 (EP) .................................. 15306530

(51) Int. Cl.
| G01N 31/00 | (2006.01) |
| G01N 33/53 | (2006.01) |
| C12Q 1/6886 | (2018.01) |
| C07K 16/30 | (2006.01) |
| A61K 39/395 | (2006.01) |
| A61K 38/50 | (2006.01) |
| A61K 31/436 | (2006.01) |
| A61K 31/155 | (2006.01) |
| A61P 35/00 | (2006.01) |
| G01N 33/574 | (2006.01) |
| C07K 16/28 | (2006.01) |

(52) U.S. Cl.
CPC .......... *C12Q 1/6886* (2013.01); *A61K 31/155* (2013.01); *A61K 31/436* (2013.01); *A61K 38/50* (2013.01); *A61K 39/39558* (2013.01); *A61P 35/00* (2018.01); *C07K 16/2887* (2013.01); *C07K 16/30* (2013.01); *C12Y 102/01012* (2013.01); *C12Y 305/01001* (2013.01); *G01N 33/57407* (2013.01); *C07K 2317/24* (2013.01); *C12Q 2600/106* (2013.01); *C12Q 2600/158* (2013.01); *G01N 2333/904* (2013.01); *G01N 2333/90203* (2013.01); *G01N 2800/52* (2013.01)

(58) Field of Classification Search
None
See application file for complete search history.

(56) References Cited

U.S. PATENT DOCUMENTS 9,879,325 B2 * 1/2018 Chiche ...................... A61P 7/06
2014/0314867 A1 10/2014 Cuenca

FOREIGN PATENT DOCUMENTS

| WO | 2006/038089 A2 | 4/2006 |
| WO | 2015/132163 A1 | 9/2015 |
| WO | WO-2015132163 A1 * | 9/2015 |

OTHER PUBLICATIONS

Chiche et al. (Leukemia, 2015, vol. 29, pp. 1163-1176) (Year: 2015).*
Inrino et al. (Journal of Molecular Diagnostics, Aug. 2004, vol. 6, N.3, pp. 217-224) (Year: 2004).*
Appel et al. (Blood, 2006, ol.107, pp. 4244-4249) (Year: 2006).*

* cited by examiner

*Primary Examiner* — Lisa V Cook
(74) *Attorney, Agent, or Firm* — W&C IP (57) ABSTRACT

Provided is an in vitro method for determining the metabolic status of a lymphoma comprising a step of determining the level of glyceraldehyde-3-phosphate dehydrogenase (GAPDH) expression in lymphoma cells, wherein a low level of GAPDH expression is indicative of oxidative phosphorylation (OXPHOS) status. Also provided is an in vitro method for predicting the responsiveness of a patient afflicted with a lymphoma to a treatment with a metabolic inhibitor selected from the group consisting of mitochondrial metabolic inhibitors and glutamine metabolism inhibitors comprising a step of determining the level of GAPDH expression in lymphoma cells obtained from said patient, wherein a low level of GAPDH expression is predictive of a response to a treatment with a metabolic inhibitor.

9 Claims, 8 Drawing Sheets

METHODS FOR DETERMINING THE METABOLIC STATUS OF LYMPHOMAS

CROSS-REFERENCE TO RELATED APPLICATIONS

This application is a national stage application of PCT/EP2016/073315 filed Sep. 29, 2016 which claims the benefit of priority to European Application 15306530.5 filed Sep. 29, 2015.

FIELD OF THE INVENTION

The invention relates to a method for determining the metabolic status of lymphomas. The invention also relates to a method for predicting the responsiveness of a patient to a treatment with a metabolic inhibitor selected from the group consisting of mitochondrial metabolic inhibitors and glutamine metabolism inhibitors.

BACKGROUND OF THE INVENTION

Lymphoma is a common cancer in the Western world. 90% of aggressive lymphomas originate from B-cells and are classified as diffuse large B-cell lymphomas (DLBCLs), a genetically heterogeneous group of tumors, the most common non-Hodgkin lymphomas. Previously, the accepted form of therapy for DLBCL was CHOP: a combination of cyclophosphamide, hydroxydaunorubicine (doxorubicin), Oncovin® (vincristine) and prednisone. In 1997, the FDA approved rituximab (Rituxan®) for treatment of aggressive Non-Hodgkin lymphomas. Combination of rituximab with CHOP demonstrated high response rate with high overall and progression-free survival (PFS), even with fewer rounds of CHOP therapy. However, it appears that patients receiving such combination have different response rates, which result in different survival times. Thus, there is a need to identify patients who would benefit from the anti-CD20 therapy such as rituximab treatment and patients who would likely not respond well to such therapy, and would need a different therapy instead.

To date, efforts to capture the molecular heterogeneity of DLBCL have relied on gene expression profiling that has uncovered coordinate signaling and survival paradigms in distinct subsets of DLBCL.

In one approach, classification framework known as cell-of-origin (COO) delineates DLBCL subsets that shared components of their transcriptional profiles with normal B-cell subtypes, including Germinal Center B-cell (GCB)-like and Activated B-cell (ABC)-like (Alizadeh et al., 2000).

In another approach, comparison of the genetic signatures across DLBCLs using genome-wide arrays and multiple clustering algorithms captured tumor-intrinsic distinctions in three separate and reproducible clusters. Groups of DLBCLs identified by this consensus cluster classification (CCC) scheme are the BCR/proliferation cluster (BCR-DLBCL) displaying up-regulation of genes encoding B-cell receptor (BCR) signaling components, the OXPHOS cluster (OXPHOS-DLBCL), which is significantly enriched in genes involved in mitochondrial oxidative phosphorylation (OXPHOS), and the host response (HR) tumors largely characterized by a brisk host inflammatory infiltrate (Monti et al., 2005).

Amongst these different subsets, OXPHOS-DLBCL represents a subset which may be selectively targeted since cancer metabolism is become a new and exciting field of biology that provides a fundamentally different approach to treating cancer. Unfortunately, until now, determining the metabolic status of a tumor, including lymphoma (i.e. determining whether a tumor rely on glycolysis or on OXPHOS) is not compatible with clinical use. Indeed, the metabolic status of a tumor in a patient is currently determined by extensive genomic and proteomic analysis, which are not compatible with clinical investigation. It results that a method easier to implement but highly reliable, and allows to determine the metabolic status of lymphoma and to stratify patient afflicted with lymphoma in order to determine which patients will have most of the chances to respond to mitochondrial metabolic inhibitors.

SUMMARY OF THE INVENTION

In a first aspect, the invention relates to an in vitro method for determining the metabolic status of a lymphoma wherein said method comprises a step of determining the level of glyceraldehyde-3-phosphate dehydrogenase (GAPDH) expression in lymphoma cells, wherein a low level of GAPDH expression is indicative of oxidative phosphorylation (OXPHOS) status.

In a second aspect, the invention relates to an in vitro method for predicting the responsiveness of a patient affected with a lymphoma to a treatment with a metabolic inhibitor selected from the group consisting of mitochondrial metabolic inhibitors and glutamine metabolism inhibitors wherein said method comprises a step of determining the level of GAPDH expression in lymphoma cells obtained from said patient, wherein a low level of GAPDH expression is predictive of a response to a treatment with a said metabolic inhibitor.

In a third aspect, the invention relates to a mitochondrial inhibitor selected from the group consisting of mitochondrial metabolic inhibitors and glutamine metabolism inhibitors as above-described for use in a method for treating a patient in need thereof, wherein said method comprises the following steps:
 a) identifying if a patient is responsive to treatment with metabolic inhibitor with the method for predicting the responsiveness according to the invention; and
 b) treating with a metabolic inhibitor the responder patient identified.

DETAILED DESCRIPTION OF THE INVENTION

The invention is based on the unexpected discovery that only GAPDH is a valuable biomarker to determine the metabolic status of the lymphoma cells in a patient leading to important implications to maximize the therapeutic use of metabolic inhibitors.

Indeed, the inventors demonstrated by using primary murin lymphoma models that amongst the different enzymes involved in glycolysis, only GAPDH enables to strictly predict the metabolic status of the lymphoma cells (Glycolytic versus OXPHOS status of said cancer cells). Interestingly, the inventors demonstrated that cancer cells expressing low levels of GAPDH are more dependent on the mitochondrial pathway to produce their energy and that they are therefore more sensitive to mitochondrial metabolic inhibitors. More particularly, the inventors showed that in contrast to B lymphomas expressing high levels of GAPDH, B lymphomas expressing low levels of GAPDH or B lymphomas silenced for GAPDH are more sensitive to the mitochondrial complex I inhibitor phenformin. In addition, B lymphoma progression is reduced upon phenformin treatment in Eµ-Myc-gapdh$^{low}$-bearing mice.

Accordingly, determining GAPDH levels which may be assessed by automated immunohistochemistry (IHC) represents an easy and convenient way to select patients that may benefit from mitochondrial inhibitors since lymphoma cells with low levels of GAPDH should be preferably targeted and killed by metabolic inhibitors.

Detecting and Prognostic Methods of the Invention

In a first aspect, the invention thus relates to an in vitro method for determining the metabolic status of a lymphoma, wherein said method comprises a step of determining the level of glyceraldehyde-3-phosphate dehydrogenase (GAPDH) expression in lymphoma cells, wherein a low level of GAPDH expression is indicative of oxidative phosphorylation (OXPHOS) status.

As used herein, the term "Glyceraldehyde-3-phosphate dehydrogenate (GAPDH)" refers to an key enzyme the glycolytic pathway which catalyzes the reaction of glyceraldehyde-3-phosphate (G3P)+NAD$^+$+Pi into 1,3 diphosphoglycerate+NADH+H$^+$. The naturally occurring GAPDH protein has an aminoacid sequence as shown in GenBank Accession number NP_001243728 and is encoded by the nucleic acid sequence provided in the GenBank database under accession number NM_001256799.

As used herein, the "oxidative phosphorylation" (OXPHOS) refers to the overall process of electron transport and ATP synthesis, and the components responsible for performing these processes are referred to as the "OXPHOS system". The components involved in OXPHOS include 5 multi-subunit protein complexes (referred to as complexes I, II, III, IV, and V), a small molecule (ubiquinone, also called coenzyme Q), and the protein cytochrome c (Cyt c). The set of proteins and small molecules involved in electron transport is referred to as the "electron transport chain" or "respiratory chain". Protons are pumped across the inner mitochondrial membrane (i.e., from the matrix to the intermembrane space) by complexes I, III, and IV. Ubiquinone, and cytochrome c function as electron carriers. Electrons from the oxidation of succinate to fumarate are channeled through this complex to ubiquinone. Complex V is ATP synthase, which is composed of a head portion, called the F1 ATP synthase (or F1), and a transmembrane proton carrier, called F0. Both F1 and F0 are composed of multiple subunits. ATP synthase can function in reverse mode in which it hydrolyzes ATP. The energy of ATP hydrolysis can be used to pump protons across the inner mitochondrial membrane into the matrix. ATP synthase is also referred to as F0-F1 ATP synthase or F0-F1 ATPase.

As used herein, the term "level expression" refers to the expression level of a gene of interest (e.g. GAPDH). It refers to the expression of the transcripts and/or proteins. The level expression of the gene of interest may in general be determined by either measuring mRNA from the cells and/or measuring expression products, such as proteins. Expression of the transcripts and/or proteins encoded by the nucleic acids described herein may be determined by any of a variety of known methods in the art. The level of GAPDH expression in cells such as lymphoma cells (i.e. B cells) obtained from the patient may be determined using any technique suitable for detecting GAPDH levels in cells. Typically, the level of GAPDH expression may be determined by quantitative PCR (qPCR), or immunohistochemistry (IHC).

Typically the B cells are obtained from a biopsy, preferably a lymph node biopsy or from a blood sample. Flow cytometry may also be used to obtain B cells. An example of method for determining the level of GAPDH expression in B cells is: Cells are permeabilized and fixed using the BD Cytofix/cytoperm solution (BD Biosciences) and incubated at 4° C. for 20 min. The cells are then washed in saponin containing buffer (BD Perm/Wash) and resuspended in the same buffer containing anti-GAPDH antibody (Abeam ab9485; dilution 1/100) and incubated for 30 min at 4° C. The cells are washed twice with the saponin-containing buffer and incubated with a Allophycocyanin (APC)-coupled anti-Rabbit antibody (dilution 1/100) for 30 min at 4° C. in the same buffer. After washing twice in the saponin-containing buffer, the cells are resuspended in PBS/2% FCS and analyzed by flow cytometry. Alternatively, the level of GAPDH expression may be determined on human formalin-fixed, paraffin-embedded DLBCL biopsies. Accordingly, sections (4 µm) are transferred to slides (X-Tra, Surgipath) and are air-dried overnight at 57° C. They are then dewaxed in xylene and rehydrated in alcohol and in distilled water, according to standard procedures. After antigen retrieval with a pH 9.0-buffered solution, sections are immunostained automatically (Autostainer Link48, Dako) according to the manufacturer's specifications (DAKO EnVison FLEX/HRP System) with a rabbit anti-GAPDH 1/500 (HPA040067 SIGMA). The reaction product is visualized by exposing sections to the 3,3'-diaminobenzidine (DAB). Sections are counterstained with hematoxylin before they are mounted.

The level expression of GAPDH measured with the methods as described above is compared to a predetermined reference value. As used herein, the term "predetermined reference value" refers to a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement in properly banked historical subject samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the expression level of the selected peptide in a group of reference, one can use algorithmic analysis for the statistic treatment of the expression levels determined in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc. Typically, using relative quantification of GAPDH mRNA by qPCR a value of 1 is attributed for the level of GAPDH mRNA expressed in normal human B cells sorted from health human blood donor. GAPDH mRNA expression in human tumors was compared to GAPDH mRNA level in healthy human B cells. The same approach was using for Eµ-Myc model to determine the level of GAPDH mRNA in B lymphomas compared to its expression in normal lymphnodes.

Typically, when the expression of GAPDH is lower than its predetermined reference value, is indicative of oxidative phosphorylation (OXPHOS) status.

Method for Predicting the Responsiveness of a Patient Affected with a Lymphoma to a Treatment with a Metabolic Inhibitor or Immune Checkpoint Inhibitor In a second aspect, the invention relates to an in vitro method for predicting the responsiveness of a patient affected with a lymphoma to a treatment with a metabolic inhibitor selected from the group consisting of mitochondrial metabolic inhibitors and glutamine metabolism inhibitors, wherein said method comprises a step of determining the level of GAPDH expression in lymphoma cells obtained from said patient, wherein a low level of GAPDH expression is predictive of a response to a treatment with a metabolic inhibitor.

The term "patient" refers to any subject (preferably human) afflicted with lymphoma.

Preferably the lymphoma is a B-cell lymphoma, including non-Hodgkin's B cell lymphoma, such as for example follicular lymphoma (FL), Burkitt lymphoma and diffuse large B-cell lymphoma (DLBCL), more preferably a DLBCL.

In one embodiment of the invention, the lymphoma cells obtained from said patient are B cells.

The method of the invention enables to determine whether a patient will be a responder or not to a treatment with a metabolic inhibitor.

As used herein, the term "responder" patient refers to a patient who shows a clinically significant relief in the disease when treated with a metabolic inhibitor such as mitochondrial metabolic inhibitor or glutamine metabolism inhibitors.

In one embodiment of the invention, the metabolic inhibitor is a mitochondrial metabolic inhibitor.

The term "mitochondrial metabolic inhibitors" refers to compounds which reduce mitochondrial activity and demonstrate varying degrees of mitochondriotoxic properties. Mitochondrial inhibitors comprise so-called uncoupling agents, which uncouple the flow of protons from ATP synthesis in mitochondria, and inhibitors that target different complexes of the electron transfer chain (ETC) in mitochondria, e.g. complex I, complex II, complex III, complex IV, and complex V of the electron transfer chain. Further compounds considered to be mitochondrial inhibitors according to the invention are mitochondriotoxic compounds targeting the mitochondrial genome. Mitochondrial inhibitors, such as mitochondrial complex I inhibitors have been described in Miyoshi 1998 and more recently in Ramsay et al., 2011.

Mitochondrial metabolic inhibitors according to the invention comprise:
  drugs used in liver or gallbladder disease with mitochondrial side effects, such as tetracycline, ibuprofen, amiodarone, pirprofen, tamoxifen, valproate, chloroquine, quinidine, chlorpromazine, ketoconazole, cyclosporine A, rifampicine, and glyburine;
  inhibitors of electron transport chain complex I, such as amytal, capsaicin, haloperidol, risperidone, rotenone, idebenone, meperidine (demerol), metformin, buformin, phenformin, bupivacaine, lidocaine, dequalininum chloride, cinnarizine, ranolazine, halothane, dantrolene, phenytoin, clofibrate, and fenofibrate;
  inhibitors of electron transport chain complex II, such as cyclophosphamide and ketoconazole;
  inhibitors of electron transport chain complex III, such as antimycin A, acetaminophen, isoflurane, and sevoflurane;
  inhibitors of electron transport chain complex IV, such as cephaloridine, cefazolin, and cefalotin;
  inhibitors of mitochondrial DNA synthesis, such as AZT (itovudidine), d4T (stavudine), ddl (didanosine), and ddC (zalcitabine);
  uncouplers of oxidative phosphorylation, such as pentamidine, indomethacin, fluoxetine, propofol, aspirin, bubivacaine, tolcapone, and dinitrophenol;
  agents which reduce molecular oxygen to superoxide via a redox mechanism, such as doxorubicin, isoniazid, gentamycin, and fluoroquinolone; and
  inhibitors of mitochondrial gene transcription, such as interferon-alpha and interferon-gamma.

In one embodiment of the invention, the mitochondrial metabolic inhibitor is a mitochondrial complex I inhibitor.

In a particular embodiment of the invention, the mitochondrial complex I inhibitor is selected from the group consisting of biguanides, rotenoids, piericidins, capsaicins, pyridinium-type inhibitor, and thiazolidinediones.

Biguanides considered are, for example, metformine, phenformin or buformin, preferably phenformin.

Alternatively, the metabolic inhibitor is glutamine metabolism inhibitor.

As used herein the term "glutamine metabolism inhibitors" refers to compounds which decrease or inhibits the glutamine pathway since in many cancer cells glutamine is the primary mitochondrial substrate and is required to maintain mitochondrial membrane potential and integrity as well as support of the NADPH production needed for redox control and macromolecular synthesis. Inhibitors of the glutamine pathway have been described in Wise et al., 2010.

Glutamine metabolism inhibitors according to the invention comprise:
  inhibitors of the glutamine synthase (GS) such as methionine sulfoximine, methionine sulfone, phosphinothricin, tabtoxinin-b-lactam, methionine sulfoximine phosphate, alpha-methyl methionine sulfoximine, alpha-ethyl methionine sulfoximine, ethionine suloximine, alpha-methyl ethionine sulfoximine, prothionine sulfoximine, alpha-methyl prothionine sulfoximine, gamma-hydroxy phosphinothricin, gamma-methyl phosphinothricin, gamma-acetoxy phosphinothricin, alpha-methyl phosphinothricin, alpha-ethyl phosphinothricin, cyclohexane phosphinothricin, cyclopentane phosphinothricin, tetrhydrofuran phosphinothricin, s-phosphonomethylhomocysteine, s-phosphonomethyl homocysteine sulfoxide, s-phosphonomethyl homocysteine sulfone, 4-(phosphonoacetyl)-L-alpha-aminobutyrate, threo-4-hydroxy-D-glutamic acid, threo-4-fluoro-D,L-glutamic acid, erythro-4-fluoro-D,L-glutamic acid, 2-amino-4-[(phosphonomethyl) hydroxyphosphinyl)]butanoic acid, alanosine, 2-amino-4-phosphono butanoic acid, 2-amino-2-methyl-4-phosphono butanoic acid, 4-amino-4-phosphono butanoic acid, 4-amino-4-(hydroxymethylphosphinyl)butanoic acid, 4-amino-4-methyl-4-phosphono butanoic acid, 4-amino-4-(hydroxymethylphosphinyl)-4-methyl butanoic acid, 4-amino-4 phosphono butanamide, 2-amido-4-phosphono butanoic acid, 2-methoxycarbonyl-4-phosphono butanoic acid, methyl 4-amino-4-phosphono butanoate and oxetin, bis-2-(5-phenylacetamido-1,3,4-thiadiazol-2-yl)ethyl sulfide.

inhibitors of cell glutamine uptake such as L-γ-glutamyl-p-nitroanilide (GPNA).

inhibitors of glutamine transporters such as ASCT2 and LAT1 compounds which decrease or inhibit blood glutamine levels such as L-asparaginase and phenylbutyrate (Buphenyl, [Ucyclyd Pharma] an FDA approved drug for the treatment of hyperammonemia in patients with acute liver failure or with congenital urea cycle disorders.)

The term "L-asparaginase" (L-ASP) refers to any enzyme that catalyzes the hydrolysis of asparagine to aspartic acid. For example, it includes bacterial forms of L-ASP, or particularly, *E. coli* forms of L-ASP. L-ASP is an enzyme drug used in combination with vincristine and dexamethasone to treat acute lymphoblastic leukemia (ALL). Thus, L-ASP from *E. coli* was the first enzyme drug used in ALL therapy and has been marketed as Elspar® in the USA or as Kidrolase® and L-asparaginase Medac® in Europe. L-ASP have also been isolated from other microorganisms, e.g., an L-ASP protein from *Erwinia chrysanthemi*, named crisantaspase that has been marketed as Erwinase®. Modified L-ASP have also been developed such as methoxy-polyethyleneglycol (mPEG) so-called pegaspargase, marketed as Oncaspar® (Enzon Inc., USA) or PEGylated L-ASP from *Erwinia* as described in the International Patent Application WO 2011/003886.

In another embodiment, the method according to the invention is suitable for predicting the responsiveness of a patient affected with a lymphoma to a treatment with an immune check point inhibitors.

As used herein, the term "immune checkpoint inhibitor" refers to molecules that totally or partially reduce, inhibit, interfere with or modulate one or more immune checkpoint proteins. As used herein, the term "immune checkpoint protein" has its general meaning in the art and refers to a molecule that is expressed by T cells in that either turn up a signal (stimulatory checkpoint molecules) or turn down a signal (inhibitory checkpoint molecules). Immune checkpoint molecules are recognized in the art to constitute immune checkpoint pathways similar to the CTLA-4 and PD-1 dependent pathways (see e.g. Pardoll, 2012. Nature Rev Cancer 12:252-264; Mellman et al., 2011. Nature 480:480-489). Examples of stimulatory checkpoint include CD27 CD28 CD40, CD122, CD137, OX40, GITR, and ICOS. Examples of inhibitory checkpoint molecules include A2AR, B7-H3, B7-H4, BTLA, CTLA-4, CD277, IDO, KIR, PD-1, LAG-3, TIM-3 and VISTA. The Adenosine A2A receptor (A2AR) is regarded as an important checkpoint in cancer therapy because adenosine in the immune microenvironment, leading to the activation of the Ata receptor, is negative immune feedback loop and the tumor microenvironment has relatively high concentrations of adenosine. B7-H3, also called CD276, was originally understood to be a co-stimulatory molecule but is now regarded as co-inhibitory. B7-H4, also called VTCN1, is expressed by tumor cells and tumor-associated macrophages and plays a role in tumour escape. B and T Lymphocyte Attenuator (BTLA) and also called CD272, has HVEM (Herpesvirus Entry Mediator) as its ligand. Surface expression of BTLA is gradually downregulated during differentiation of human CD8+ T cells from the naive to effector cell phenotype, however tumor-specific human CD8+ T cells express high levels of BTLA. CTLA-4, Cytotoxic T-Lymphocyte-Associated protein 4 and also called CD152. Expression of CTLA-4 on Treg cells serves to control T cell proliferation. IDO, Indoleamine 2,3-dioxygenase, is a tryptophan catabolic enzyme. A related immune-inhibitory enzymes. Another important molecule is TDO, tryptophan 2,3-dioxygenase. IDO is known to suppress T and NK cells, generate and activate Tregs and myeloid-derived suppressor cells, and promote tumour angiogenesis. KIR, Killer-cell Immunoglobulin-like Receptor, is a receptor for MHC Class I molecules on Natural Killer cells. LAG3, Lymphocyte Activation Gene-3, works to suppress an immune response by action to Tregs as well as direct effects on CD8+ T cells. PD-1, Programmed Death 1 (PD-1) receptor, has two ligands, PD-L1 and PD-L2. This checkpoint is the target of Merck & Co.'s melanoma drug Keytruda, which gained FDA approval in September 2014. An advantage of targeting PD-1 is that it can restore immune function in the tumor microenvironment. TIM-3, short for T-cell Immunoglobulin domain and Mucin domain 3, expresses on activated human CD4+ T cells and regulates Th1 and Th17 cytokines. TIM-3 acts as a negative regulator of Th1/Tc1 function by triggering cell death upon interaction with its ligand, galectin-9. VISTA, Short for V-domain Ig suppressor of T cell activation, VISTA is primarily expressed on hematopoietic cells so that consistent expression of VISTA on leukocytes within tumors may allow VISTA blockade to be effective across a broad range of solid tumors. Tumor cells often take advantage of these checkpoints to escape detection by the immune system. Thus, inhibiting a checkpoint protein on the immune system may enhance the anti-tumor T-cell response.

In some embodiments, an immune checkpoint inhibitor refers to any compound inhibiting the function of an immune checkpoint protein. Inhibition includes reduction of function and full blockade.

In some embodiments, the immune checkpoint inhibitor could be an antibody, synthetic or native sequence peptides, small molecules or aptamers which bind to the immune checkpoint proteins and their ligands.

In a particular embodiment, the immune checkpoint inhibitor is an antibody.

As used herein, the term "antibody" is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/1 1 161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments. In some embodiments, the antibody is a "chimeric" antibody as described in U.S. Pat. No. 4,816,567. In some embodiments, the antibody is a humanized antibody, such as described U.S. Pat. Nos. 6,982, 321 and 7,087,409. In some embodiments, the antibody is a human antibody. A "human antibody" such as described in U.S. Pat. Nos. 6,075,181 and 6,150,584. In some embodiments, the antibody is a single domain antibody such as described in EP 0 368 684, WO 06/030220 and WO 06/003388.

In a particular embodiment, the immune checkpoint inhibitor is a monoclonal antibody. Monoclonal antibodies can be prepared and isolated using any technique that provides for the production of antibody molecules by continuous cell lines in culture. Techniques for production and isolation include but are not limited to the hybridoma technique, the human B-cell hybridoma technique and the EBV-hybridoma technique. Typically, antibodies are directed against A2AR, B7-H3, B7-H4, BTLA, CTLA-4, CD277, IDO, KIR, PD-1, LAG-3, TIM-3 or VISTA.

In a particular embodiment, the immune checkpoint inhibitor is an anti-PD-1 antibody such as described in WO2011082400, WO2006121168, WO2015035606, WO2004056875, WO2010036959, WO2009114335, WO2010089411, WO2008156712, WO2011110621, WO2014055648 and WO2014194302. Examples of anti-PD-1 antibodies which are commercialized: Nivolumab (Opdivo®, BMS), Pembrolizumab (also called Lambrolizumab, KEYTRUDA® or MK-3475, MERCK).

In some embodiments, the immune checkpoint inhibitor is an anti-PD-L1 antibody such as described in WO2013079174, WO2010077634, WO2004004771, WO2014195852, WO2010036959, WO2011066389, WO2007005874, WO2015048520, U.S. Pat. No. 8,617,546 and WO2014055897. Examples of anti-PD-L1 antibodies which are on clinical trial: Atezolizumab (MPDL3280A, Genentech/Roche), Durvalumab (AZD9291, AstraZeneca), Avelumab (also known as MSB0010718C, Merck) and BMS-936559 (BMS).

In some embodiments, the immune checkpoint inhibitor is an anti-PD-L2 antibody such as described in U.S. Pat. No. 7,709,214, U.S. Pat. No. 7,432,059 and U.S. Pat. No. 8,552,154.

In the context of the invention, the immune checkpoint inhibitor inhibits Tim-3 or its ligand.

In a particular embodiment, the immune checkpoint inhibitor is an anti-Tim-3 antibody such as described in WO03063792, WO2011155607, WO2015117002, WO2010117057 and WO2013006490.

In some embodiments, the immune checkpoint inhibitor is a small organic molecule.

The term "small organic molecule" as used herein, refers to a molecule of a size comparable to those organic molecules generally used in pharmaceuticals. The term excludes biological macro molecules (e. g. proteins, nucleic acids, etc.). Typically, small organic molecules range in size up to about 5000 Da, more preferably up to 2000 Da, and most preferably up to about 1000 Da.

Typically, the small organic molecules interfere with transduction pathway of A2AR, B7-H3, B7-H4, BTLA, CTLA-4, CD277, IDO, KIR, PD-1, LAG-3, TIM-3 or VISTA.

In a particular embodiment, small organic molecules interfere with transduction pathway of PD-1 and Tim-3. For example, they can interfere with molecules, receptors or enzymes involved in PD-1 and Tim-3 pathway.

In a particular embodiment, the small organic molecules interfere with Indoleamine-pyrrole 2,3-dioxygenase (IDO) inhibitor. IDO is involved in the tryptophan catabolism (Liu et al 2010, Vacchelli et al 2014, Zhai et al 2015). Examples of IDO inhibitors are described in WO 2014150677. Examples of IDO inhibitors include without limitation 1-methyl-tryptophan (IMT), β-(3-benzofuranyl)-alanine, β-(3-benzo(b)thienyl)-alanine), 6-nitro-tryptophan, 6-fluoro-tryptophan, 4-methyl-tryptophan, 5-methyl tryptophan, 6-methyl-tryptophan, 5-methoxy-tryptophan, 5-hydroxy-tryptophan, indole 3-carbinol, 3,3'-diindolylmethane, epigallocatechin gallate, 5-Br-4-Cl-indoxyl 1,3-diacetate, 9-vinylcarbazole, acemetacin, 5-bromo-tryptophan, 5-bromoindoxyl diacetate, 3-Amino-naphtoic acid, pyrrolidine dithiocarbamate, 4-phenylimidazole a brassinin derivative, a thiohydantoin derivative, a (3-carboline derivative or a brassilexin derivative. In a particular embodiment, the IDO inhibitor is selected from 1-methyl-tryptophan, β-(3-benzofuranyl)-alanine, 6-nitro-L-tryptophan, 3-Amino-naphtoic acid and β-[3-benzo(b)thienyl]-alanine or a derivative or prodrug thereof.

In a particular embodiment, the inhibitor of IDO is Epacadostat, (INCB24360, INCB024360) has the following chemical formula in the art and refers to —N-(3-bromo-4-fluorophenyl)-N'-hydroxy-4-{[2-(sulfamoylamino)-éthyl]amino}-1,2,5-oxadiazole-3 carboximidamide:

In a particular embodiment, the inhibitor is BGB324, also called R428, such as described in WO2009054864, refers to 1H-1,2,4-Triazole-3,5-diamine, 1-(6,7-dihydro-5H-benzo[6,7]cyclohepta[1,2-c]pyridazin-3-yl)-N3-[(7S)-6,7,8,9-tetrahydro-7-(1-pyrrolidinyl)-5H-benzocyclohepten-2-yl]- and has the following formula in the art:

In a particular embodiment, the inhibitor is CA-170 (or AUPM-170): an oral, small molecule immune checkpoint antagonist targeting programmed death ligand-1 (PD-L1) and V-domain Ig suppressor of T cell activation (VISTA) (Liu et al 2015). Preclinical data of CA-170 are presented by Curis Collaborator and Aurigene on November at ACR-NCI-EORTC International Conference on Molecular Targets and Cancer Therapeutics.

In some embodiments, the immune checkpoint inhibitor is an aptamer.

Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by Exponential enrichment (SELEX) of a random sequence library. The random sequence library is obtainable by combinatorial chemical synthesis of DNA. In this library, each member is a linear oligomer, eventually chemically modified, of a unique sequence.

Typically, the aptamers are directed against A2AR, B7-H4, BTLA, CTLA-4, CD277, IDO, KIR, PD-1, LAG-3, TIM-3 or VISTA.

In a particular embodiment, aptamers are DNA aptamers such as described in Prodeus et al 2015. A major disadvantage of aptamers as therapeutic entities is their poor pharmacokinetic profiles, as these short DNA strands are rapidly removed from circulation due to renal filtration. Thus, aptamers according to the invention are conjugated to with high molecular weight polymers such as polyethylene glycol (PEG). In a particular embodiment, the aptamer is an anti-PD-1 aptamer. Particularly, the anti-PD-1 aptamer is MP7 pegylated as described in Prodeus et al 2015.

Therapeutic Methods of the Invention

After being tested for responsiveness to a treatment with a metabolic inhibitor such as a mitochondrial metabolic inhibitor, the patients may be prescribed with said metabolic inhibitor or if the metabolic inhibitor treatment already started, the metabolic inhibitor treatment may be continued.

Accordingly, the invention relates to an a metabolic inhibitor selected from the group consisting of mitochondrial metabolic inhibitors and glutamine metabolism inhibitors as above-described for use in a method for treating a patient in need thereof, wherein said patient has been identified as responsive with the method for predicting the responsiveness according to the invention.

In a third aspect, the invention relates to a metabolic inhibitor selected from the group consisting of mitochondrial metabolic inhibitors and glutamine metabolism inhibitors for use in a method for treating a patient in need thereof, wherein said method comprises the following steps:
 a) identifying if a patient is responsive to treatment with metabolic inhibitor with the method for predicting the responsiveness according to the invention; and
 b) treating with a metabolic inhibitor the responder patient identified.

The invention also relates to a method for treating a patient in need thereof with a mitochondrial inhibitor selected from the group consisting of mitochondrial metabolic inhibitors and glutamine metabolism inhibitors, wherein said method comprises the following steps:
 a) identifying if a patient is responsive to treatment with a metabolic inhibitor with the method for predicting the responsiveness according to the invention; and
 b) treating with a metabolic inhibitor the responder patient identified.

The invention also relates to a method for treating a patient in need thereof with an immune checkpoint inhibitor, wherein said method comprises the following steps:
 a) identifying if a patient is responsive to treatment with an immune checkpoint inhibitor with the method for predicting the responsiveness according to the invention; and
 b) treating with an immune checkpoint inhibitor the responder patient identified.

The method according to the invention, wherein, the patient suffers from a lymphoma. As used herein, the term "lymphoma" refers to a group of blood cell tumours that develop from lymphatic cells. The two main categories of lymphomas are Hodgkin lymphomas (HL) and the non-Hodgkin lymphomas (NHL). In the context of the invention, the patient suffers from non-Hodgkin lymphomas. Non-Hodgkin lymphomas, also known as non-Hodgkin refers to a group of blood cancers that include any kind of lymphoma except Hodgkin's lymphomas. Types of NHL vary significantly in their severity, from slow growing to very aggressive types. In a particular embodiment, the patient suffers from a diffuse large B-cell lymphoma (DLBCL) which is the most common non-Hodgkin's lymphoma.

The invention will be further illustrated by the following figures and examples. However, these examples and figures should not be interpreted in any way as limiting the scope of the present invention.

FIGURES

FIG. 1: Mouse primary Eµ-Myc lymphomas express different levels of GAPDH. A. The relative levels of gapdh (left) and ldh-a (right) mRNA were determined by quantitative PCR in Eµ-Myc-gapdh$^{high}$ clones (n=4 independent clones) and in Eµ-Myc-gapdh$^{low}$ clones (n=5 independent clones). B. Quantification of GAPDH, HK2, ENO1, PKM2, PDK1 expression levels relative to Erk2 expression in Eµ-Myc-gapdh$^{high}$ (n=4) and Eµ-Myc-gapdh$^{low}$ (n=5) lymphomas (GAPDH: glyceraldehyde-3-phosphate dehydrogenase; HK2: hexokinase 2; ENO1: enolase1; PKM2: pyruvate kinase M2; PDK1: pyruvate dehydrogenase kinase 1). The presented data are the means of 3 independent experiments expressed as mean±SD. *$p<0.05$, ***$p<0.001$

FIG. 3: Compared to Eµ-Myc-gapdh$^{high}$, Eµ-Myc-gapdh$^{low}$ lymphomas are more sensitive to the mitochondrial complex I inhibitor, Phenformin and to glutamine/asparagine hydrolysis. A. EµMyc-gapdh$^{high}$ (n=3 independent clones) and Eµ-Myc-gapdh$^{low}$ (n=3 independent clones) cells were seeded in the presence or absence (Ctl) of phenformin (Phen, 200 µM) for 24 hours. Cell death was determined by DAPI staining and analyzed by FACS. B. The proliferation index was measured in 2 independent Eµ-Myc-gapdh$^{low}$ (clones #E and #G, upper panel) and in 2 independent Eµ-Myc-gapdh$^{high}$ (clones #B and C, lower panel). C. Eµ-Myc-gapdh$^{high}$ (n=3 independent clones) and Eµ-Myc-gapdh$^{low}$ (n=3 independent clones) cells were seeded in the presence or absence (Ctl) of L-asparaginase (L-asp 0.3 UI/ml; 1.0 UI/ml) for 24 hours. Cell death was determined by DAPI staining and analyzed by flow cytometry.

The presented data are the means of at least 3 independent experiments expressed as mean±SD. $p<0.01$, *$p<0.005$.

FIG. 4: Specific silencing of GAPDH sensitizes Eµ-Myc-gapdh$^{high}$ lymphomas to phenformin and L-asparaginase. A. Eµ-Myc-gapdh$^{high}$ cells silenced (shgapdh) or not (shctl) for gapdh were seeded in the presence or absence of 100 µM of phenformin for 24 and 48 hours. Cells were then labeled with DAPI (Molecular Probes; 0.5 µg/mL) and analyzed immediately by flow cytometry. B. The proliferation index was measured after 24 and 48 hours of phenformin treatment (50 µM) in Eµ-Myc-gapdh$^{high}$ cells silenced (shgapdh) or not (shctl) for gapdh cells. C. Eµ-Myc-gapdh$^{high}$ cells silenced (shgapdh) or not (shctl) for gapdh were seeded in the presence or absence of L-asparaginase (0.3 UI/ml) for 24 hours. Cells were then labeled with DAPI (Molecular Probes; 0.5 µg/mL) and analyzed by flow cytometry.

TABLE 1

Effect of combined mitochondrial inhibitors on the therapeutic response of R-CHOP-refractory DLBCL expressing low or high level of GAPDH at diagnosis (clinical trial KTMR). Nine R-CHOP refractory Myc+ -DLBCL patients were enrolled in a new clinical protocol which combined L-asparaginase, Torisel (mTOR inhibitor), Metformine and Rituximab. Out of nine, four patients experienced toxicity and were removed from the study. Immunohistochemical staining of GAPDH was performed on tumor sections obtained from biopsies at diagnosis to determine whether GAPDH could be used as a predictive marker of KTMR therapeutic response.

| GAPDH expression (IHC) - biopsies at diagnosis | L-asparaginase + Torisel + Metformine + Rituximab | | |
|---|---|---|---|
| | Progression | Partial Response | Complete Response |
| GAPDH high | 0 | 1 | 0 |
| % | 0 | 100 | 0 |
| GAPDH low | 1 | 0 | 3 |
| % | 25 | 0 | 75 |

4 patients were out of the study for toxicity reasons

Effect of combined mitochondrial inhibitors on the therapeutic response of R-CHOP-refractory DLBCL displaying low or high GAPDH expression at diagnosis (n=9).

Example

Material & Methods

Cell Culture:

Mouse primary Eµ-Myc clones (B lymphoma cells) obtained from lymphomas of different C57BL/6 Eµ-Myc transgenic mice were isolated as described previously (Lindemann et al., 2007) and maintained in DMEM supplemented with 10% FCS, 2-mercaptoethanol (50 µM), L-asparagin (0.37 mM) and HEPES (pH 7.4, 10 mM). C57BL/6 Eµ-Myc transgenic mice were purchased from the Jackson Laborator.

Reagents and Antibodies:

Rabbit anti-GAPDH was from (Abcam, Cambridge, UK), mouse anti-Erk2 was from Santa Cruz Biotechnology (Santa Cruz, Calif., USA). Other antibodies were from Cell Signaling Technology (Beverly, Mass., USA). Mitochondrial complex I inhibitor, phenformin was from Sigma.

Plasmids:

Complementary sense and antisense oligonucleotides were annealed and into BglII/HindIII-cut pSUPER retro-.Neo+GFP vector (oligoengine) to produce short hairpin RNA (shRNA) targeting mouse gapdh (shgapdh). shRNA targeting luciferase was used as a control shRNA (shctl).

ATP Analysis:

ATP was measured using the Promega Cell Titer Glo kit. In summary, 20.000 cells were re-suspended in 80 µL and distributed in a 96 well plate. Cells were then treated in triplicates with control (PBS), oligomycin A, or sodium iodoacetate both alone or in combination with oligomycin A. Following a 1-hour incubation, 100 uL of cell titer Glo reaction mix were added to each well for a final volume of 200 uL. Plates were then analyzed for luminescence with a Luminoscan. By comparing the different conditions, global ATP and percentages of both glycolytic and mitochondrial ATP were determined.

RNA Extraction and Real-Time Quantitative PCR:

Total RNA was extracted from cells using the RNA extraction kit (Qiagen) according to the manufacturer's instructions. Total RNA (2 µg) was added to 20 µl reverse transcription-PCR using the Omniscript kit (Qiagen). The relative mRNA expression level of gapdh and ldh-a (mouse) were obtained by real-time quantification PCR (qPCR), using the TaqMan PCR Master Mix (Eurogentec) and TaqMan assay primer set (Applied Biosystems, Foster City, Calif.) on the 7500 Fast and the Step One (Applied Biosystems) according to the manufacturer's instructions (sequences provided upon request). For in vitro experiment, all samples were normalized to 18s.

Western Blot Analysis:

Mouse primary Eµ-Myc cells were washed and lysed in laemmli buffer. Proteins (40 µg) were separated on 8% to 12% SDS polyacrilamide gels and transferred onto polyvinylidene difluoride membranes (Millipore). Membranes were then blotted with antibody corresponding to the indicated proteins. Immunoreactive bands were detected with a horseradish peroxidase (HRP) anti-mouse (Dako) or anti-rabbit (Cell Signaling) by enhanced chemiluminescence (Pierce). When indicated, Western blot quantification was made using ImageJ software.

Proliferation Assay:

Eµ-Myc cells ($0.2 \times 10^6$) were seeded in 96 well-plates in the presence or absence of 50 µM of Phenformin for 0, 24 and 48 hours. Number of living and dead cells was counted using DAPI staining exclusion by flow cytometry (MACSQuant Analyser, Miltenyi Biotec). Proliferation index were calculated by dividing the number of living cells obtained for each day by the one obtained the day of seeding (day 0).

Cell Death Assay:

Eµ-Myc cells ($0.2 \times 10^6$) were seeded in 96 well-plates in the presence or absence of 200 µM of phenformin (Sigma) for 24 hours and 48 hours. Cells were then labeled with DAPI (Molecular Probes; 0.5 µg/mL) and analyzed immediately by flow cytometry using a MACSQuant Analyzer (Miltenyi Biotec).

Animal Studies:

Lymphoma transfer of a isolated Eµ-Myc clone was realized into syngeneic, nontransgenic, 6-week-old C57BL/6 females by tail vein injection of $0.1 \times 10^6$ viable Eµ-Myc lymphoma cells per recipient mouse (in 150 µL of sterile PBS). Phenformin treated group received 200 mg/kg/day phenformin in the drinking water for 12 days. Phenformin powder was dissolved every two days in the drinking water, taking into account the mouse body weight and the volume of water consumed each day. Untreated mice (controls) received water (n=10 mice/group). Food was given ad libitum. The first signs of the pathology were determined by inguinal lymph node palpation and analyses of blood sample with Hemavet 950FS (Drew Scientific, INC, France). Progression-free survival was determined by the time between the iv injection of the cell and the appearance of enlarged lympho nodes. Lymphoma-bearing animals were killed by cervical dislocation as soon as they presented signs of illness. Upon sacrifice all lymph node tumors and spleen are immediately collected and weighted. All mice were maintained in specific pathogen-free conditions and experimental procedures were approved by the Institutional Animal Care and Use Committee and by the regional ethics committee (PEA232 from Comité Institutionnel d'Ethique Pour l'Animal de Laboratoire—AZUR).

Isolation of Human Tumor Cells from Patient Biopsies:

Tumor biopsy was incubated in RPMI supplemented with 2% of FCS, DNAse (10 µg/ml) and collagenase (0.1 mg/ml) for 5 min at 37° C. Tumor cells were then dissociated and incubated in the presence of red blood cell lysis buffer for 1 min. After washing, cells were counted and immediately analyzed for glycolytic vs OxPhos ATP, gapdh mRNA levels (qPCR). Cells were also stained for 30 min with an anti-CD20 antibody (eBioscience, 1/100) to determine the proportion of B cells within the tumor.

Clinical Trial KTMR (Kidrolas-Torisel-Metformine-Rituximab):

Nine R-CHOP refractory Myc+-DLBCL patients with adequate performance status and organ functions were enrolled in a new clinical protocol targeting tumor metabolism. Treatment combined L-asparaginase (Kidrolase, 6000 IU/ml) on days 1, 3, 5, 7, 9, 11 and 13, mTOR inhibitor (Torisel 75 mg/week) on days 1, 7 and 14 and Rituximab (375 mg/m2) on days 1 and 7 of each cycle. In between two cycles of treatment patients received Metformin daily (1000 mg/day). Four patients experienced toxicity and were removed from the study. Three patients completed four cycles of treatment and one patient completed two cycles in complete response. Median duration of response was 6 months (range, 4-6 mo).

Immunohistochemical Staining of GAPDH:

Sections (3 µm) of formalin-fixed, paraffin-embedded DLBCL biopsies were treated using standard procedures and were immunostained (using Dako manufacturer instructions) for the expression of GAPDH (Prestige, Sigma, 1/500). GAPDH staining was then scored based on the GAPDH intensity and the percentage of stained cells) to identify GAPDH low and GAPDH high lymphomas.

Statistical Analysis:

Continuous variables and binomial variables, expressed as mean (s.d.), were analyzed with Student's t-test or one-way analysis of variance and compared, respectively, between groups with Fisher's exact test or $\chi 2$ test. Continuous variables (proliferation index), expressed as mean (s.d.) after log transformation, were analyzed with linear regression and compared between groups with Fisher's exact test. For time-to-event variables, the survival functions were estimated with Kaplan-Meier method and compared with log-rank tests. All statistical analyses were done with R project software (version 2.15.1). A p-value of less than 0.05 was considered to indicate statistical significance (*$p<0.05$, $p<0.01$ and *$p<0.001$).

Results

We showed that, in contrast to B lymphomas expressing high levels of GAPDH, B lymphomas expressing low levels of GAPDH or B lymphomas silenced for GAPDH are more sensitive to the mitochondrial complex I inhibitor phenformin. In addition, B lymphoma progression is reduced upon phenformin treatment in Eµ-Myc-gapdh$^{low}$-bearing mice.

Figure 1A:
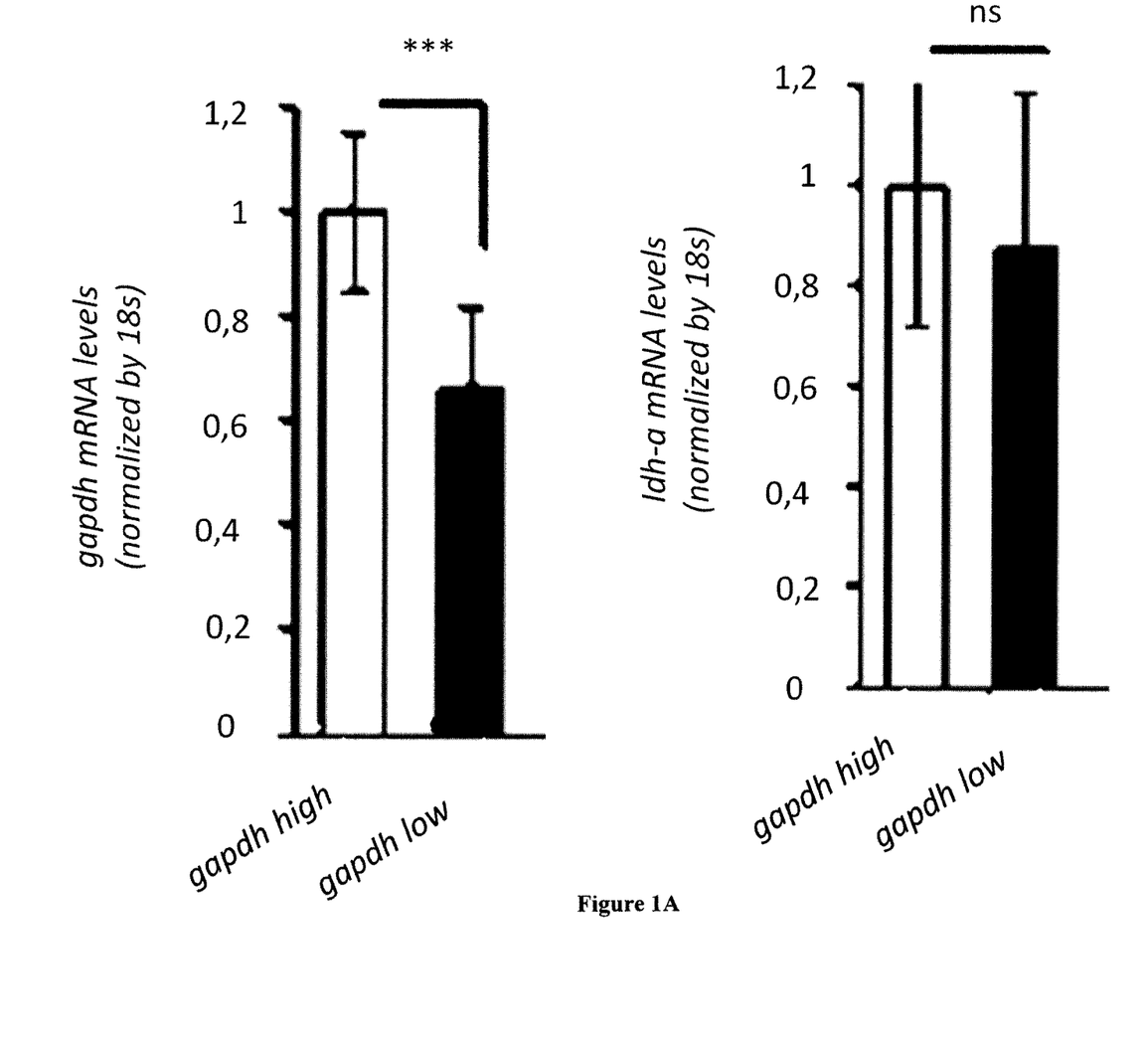
Figure 1B:
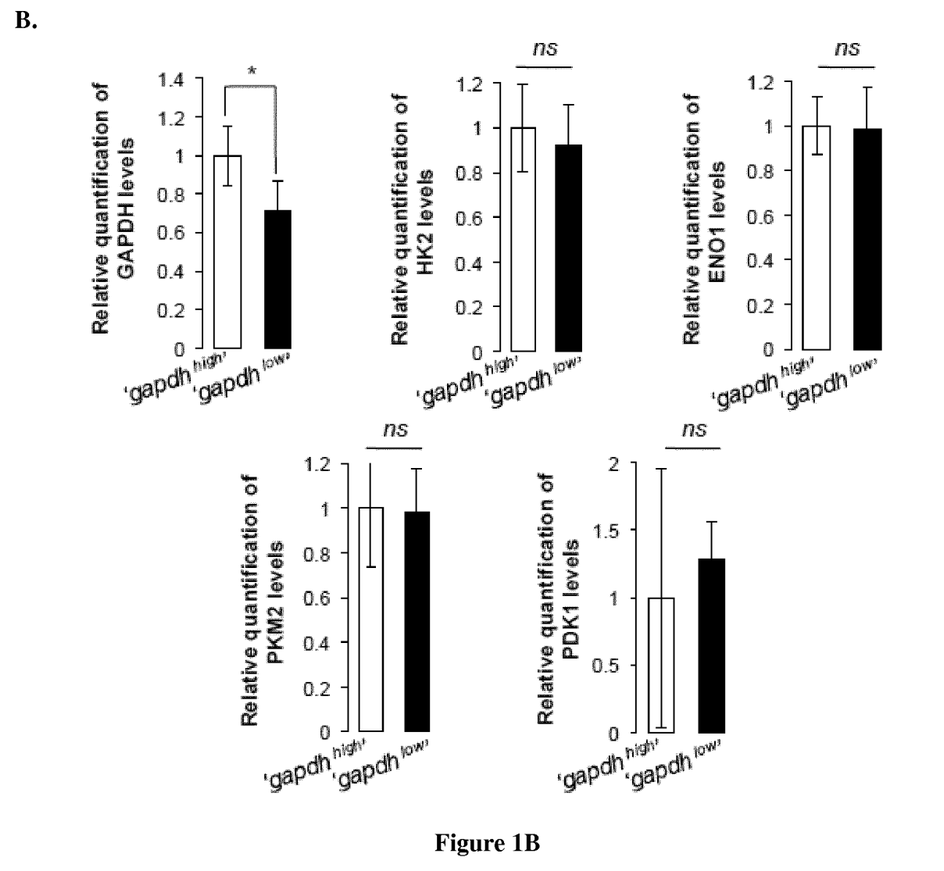

We first demonstrate that mouse primary Eµ-Myc lymphomas express different levels of gapdh mRNA (FIG. 1A)

and GAPDH protein (FIG. 1B), while the other glycolytic enzymes such as HKII, ENO1, LDH-A, PKM2 and PDK1 are expressed to the same extent (FIGS. 1A and 1B).

Figure 2:
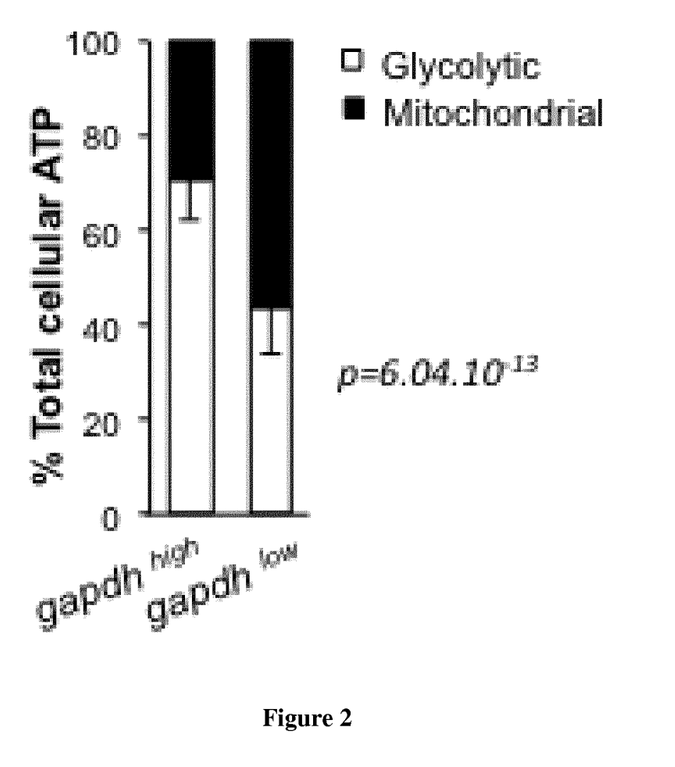
FIG. 2: Eµ-Myc-gapdh$^{low}$ clones have a mitochondrial OXPHOS phenotype compared to Eµ-Myc-gapdh$^{high}$ clones. Mitochondrial and glycolytic ATP production were measured in Eµ-Myc-gapdh$^{low}$ (n=5 independent clones) and Eµ-Myc-gapdh$^{high}$ (n=4 independent clones) clones as a percentage of total ATP production by the cells. The presented data are the means of 3 independent experiments.
Figure 3A:
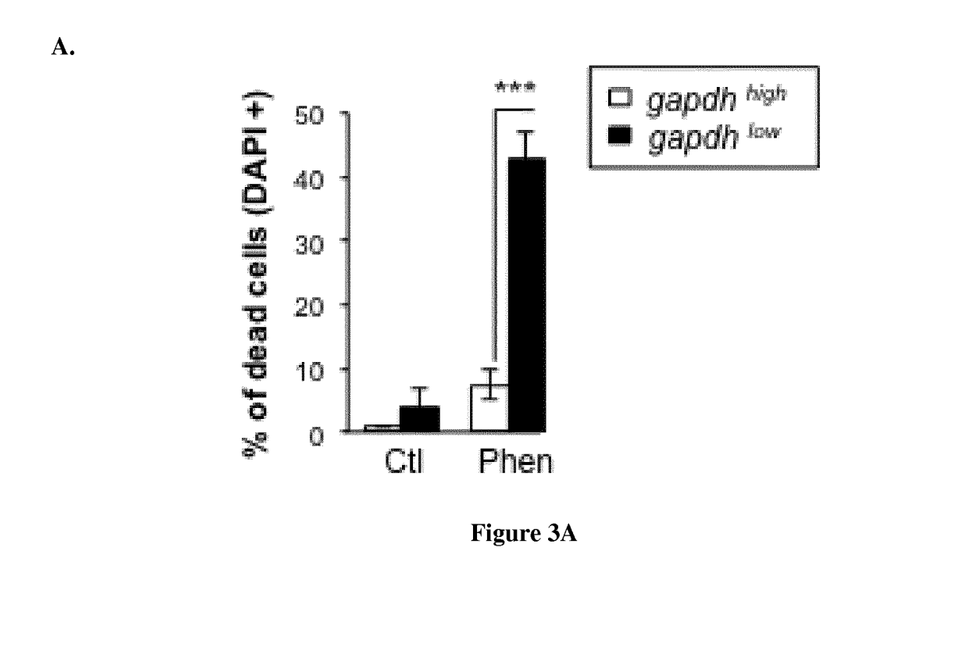
Figure 3B:
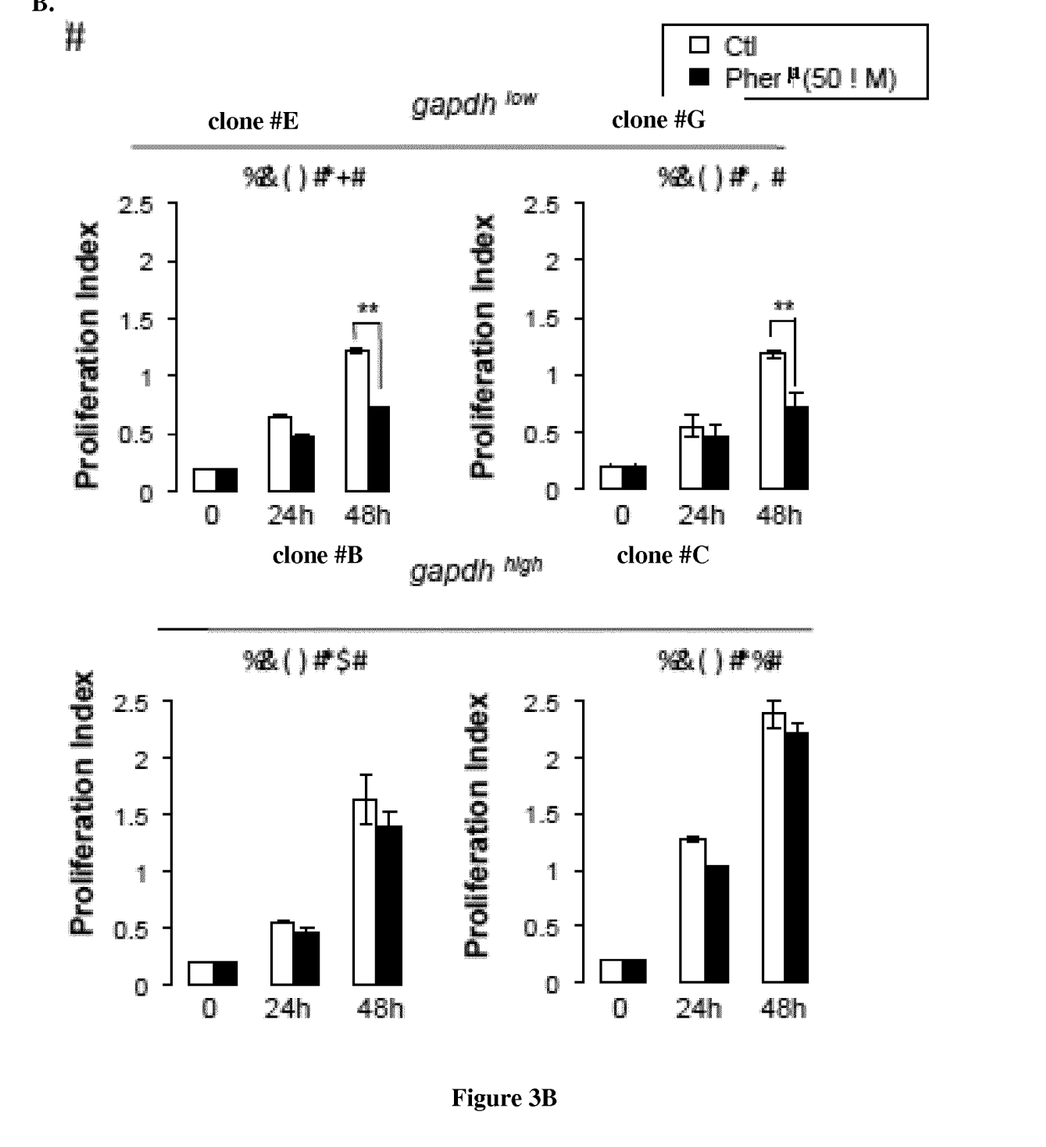
Figure 3C:
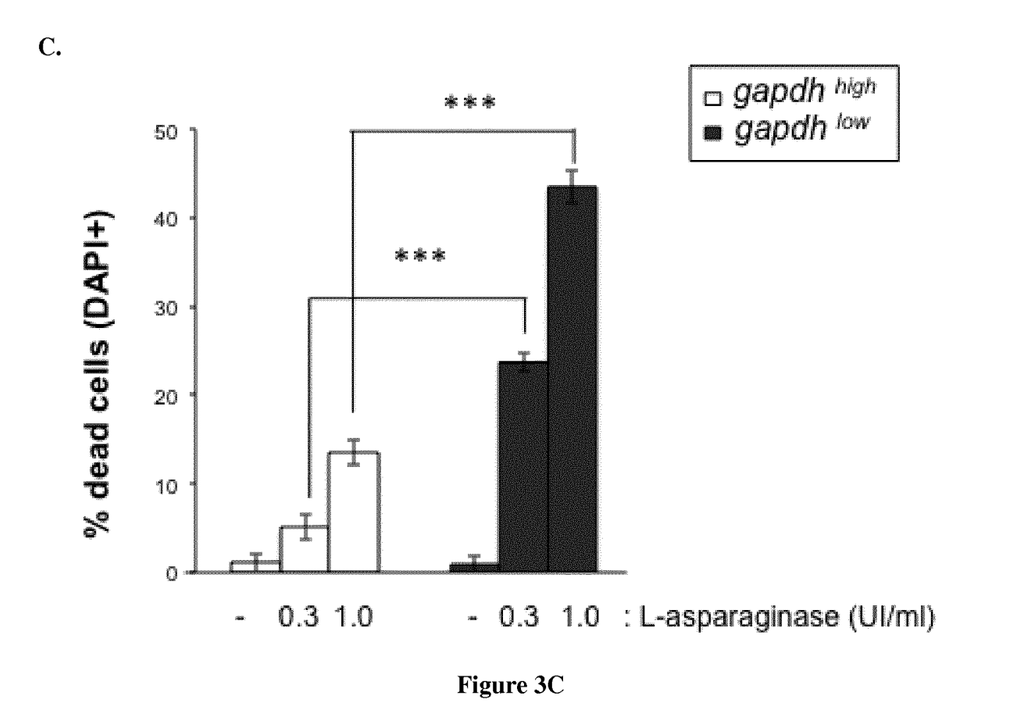
Figure 4:
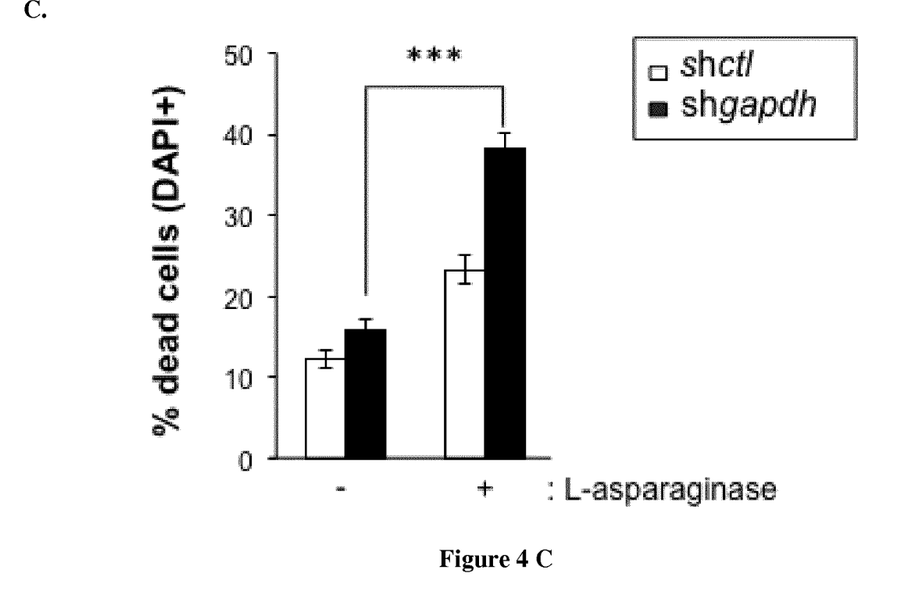
Figure 4A:
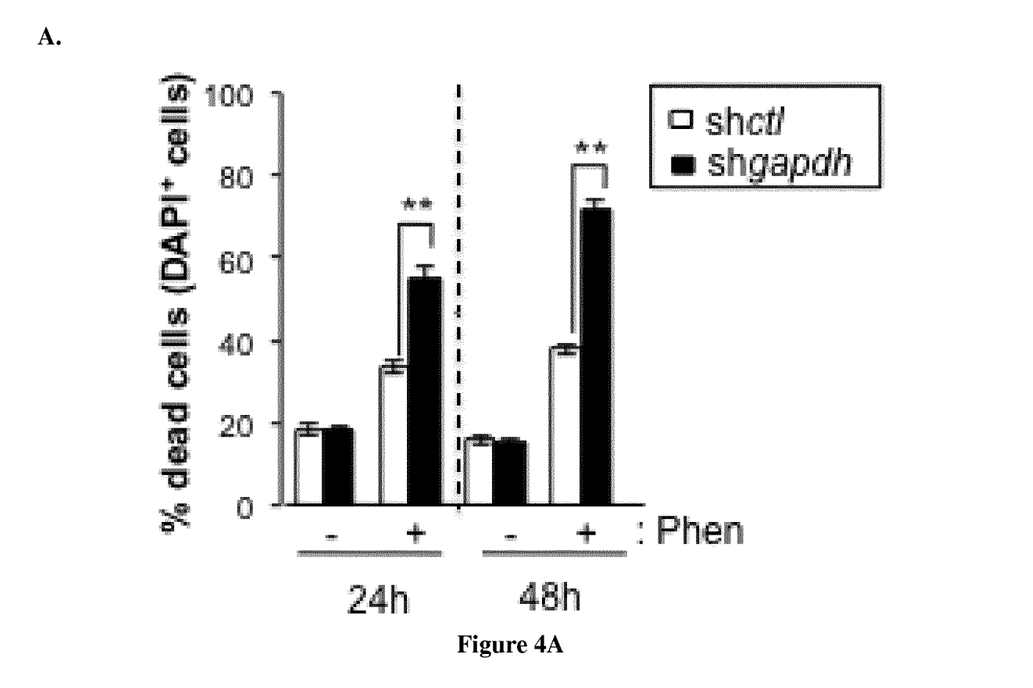
Figure 4B:
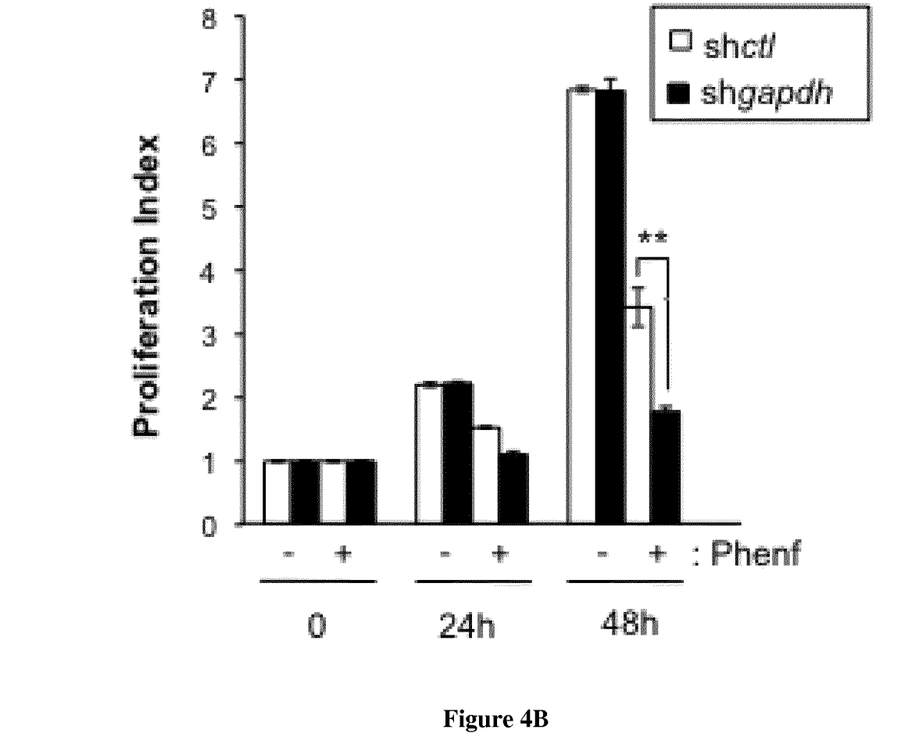
Figure 5:
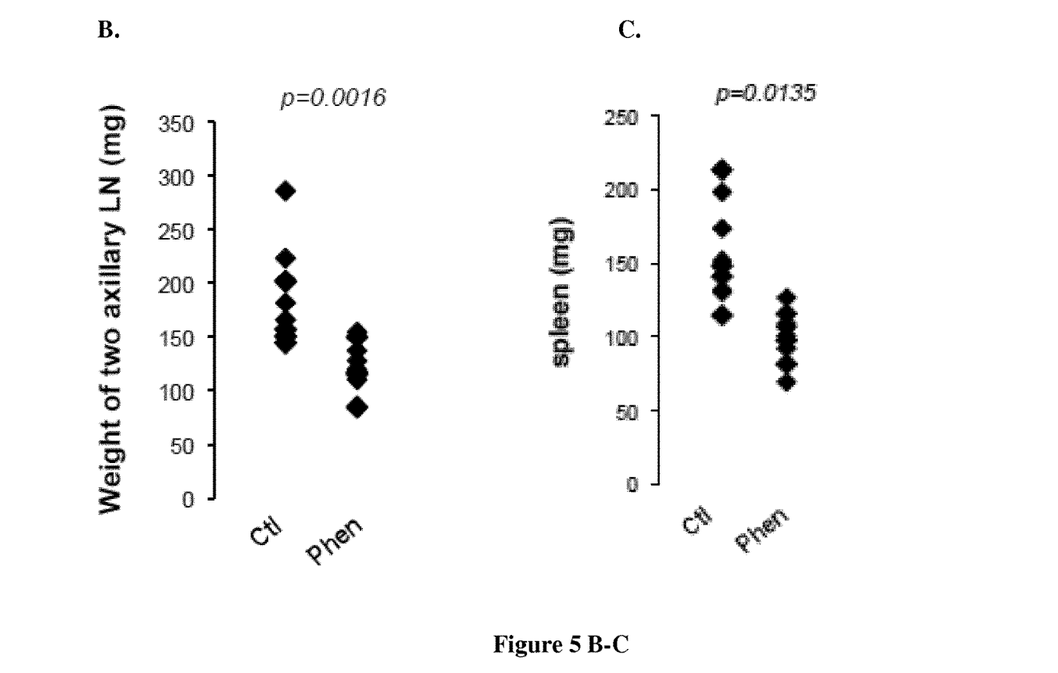
FIG. 5: Phenformin reduced lymphomas progression in Eµ-Myc-gapdh$^{low}$-bearing mice. A. Kaplan-Meier curves of progression-free survival of syngenic C57BL/6 mice intravenously injected with primary Eµ-Myc-gapdh$^{low}$ cells and treated or not (Ctl) with 200 mg/kg/day of Phenformin for 12 days (n=10 mice per group). B. C. Upon sacrifice of the animals, two axillary lymph nodes (B.) and the spleen (C.) were weighted (n=10 per group).
Figure 5A:
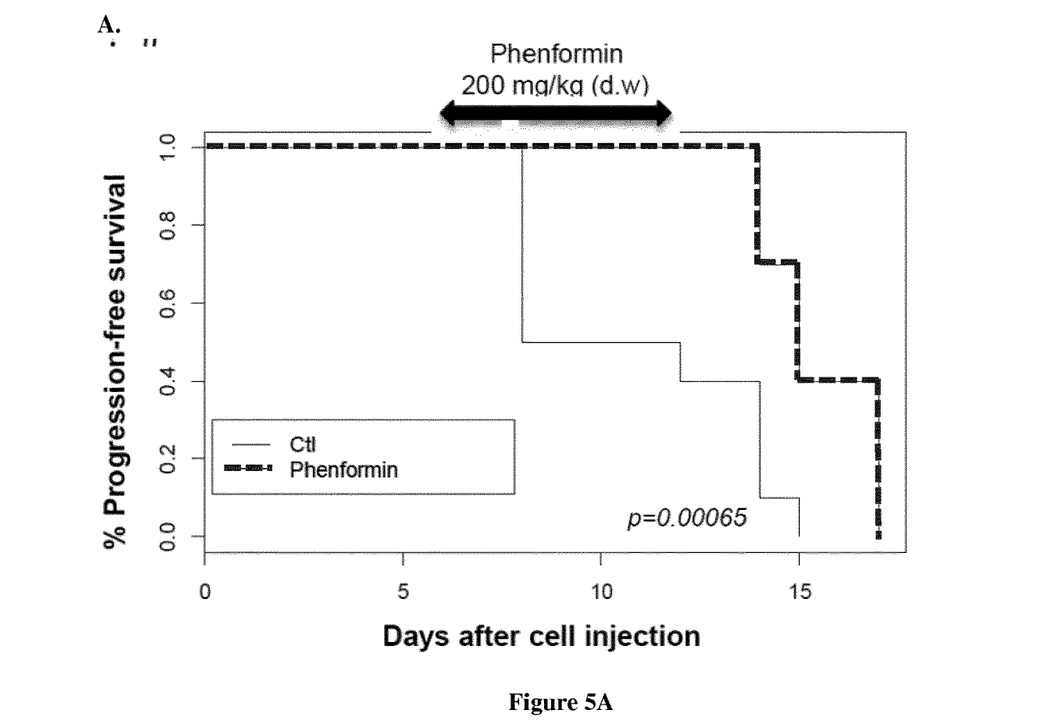
Figure 6:
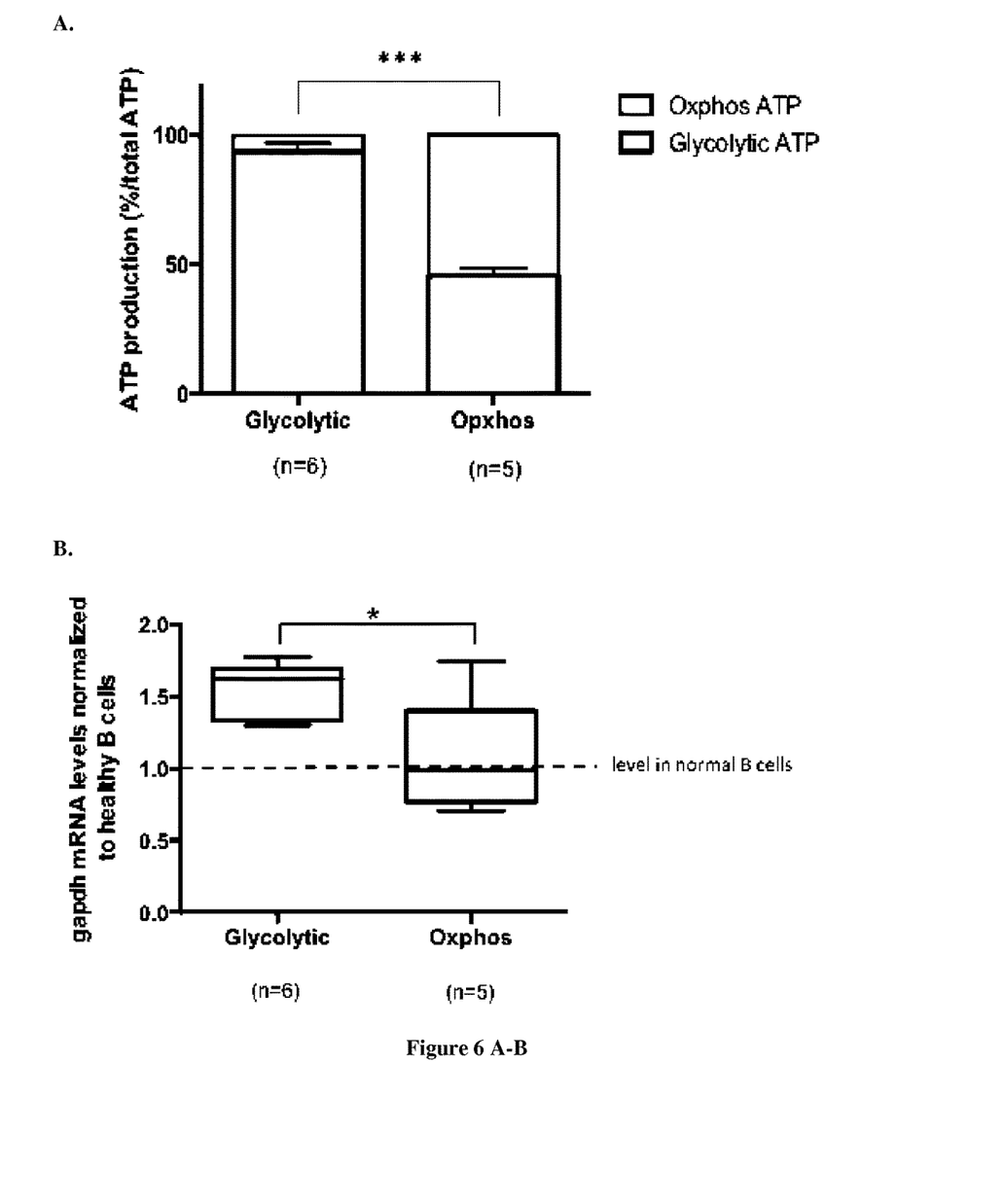
FIG. 6: Follicular lymphomas relying on OxPhos metabolism for energy production express low levels of gapdh mRNA. A. Mitochondrial (OxPhos) and glycolytic ATP were measured as a percentage of total cellular ATP produce by the tumor cells, immediately after cell dissociation of freshly harvested biopsies diagnosed as follicular lymphomas (displaying at least 70% of B cells). B. Real time qPCR analysis of gapdh mRNA levels from follicular lymphomas relying on glycolysis (n=6) or OxPhos (n=5) for ATP production. Transcript levels were determined relative to cyclophilin-A (ppia) mRNA levels. gapdh mRNA levels expressed in tumor biopsies were then normalized to that expressed in normal B cells.

In contrast to Eµ-Myc-gapdh$^{high}$ clones which mainly produce glycolytic ATP (70% glycolytic ATP and 30% of mitochondrial ATP), we demonstrated that Eµ-Myc-gapdh$^{low}$ clones produce 50 to 60% of mitochondrial (OxPhos) ATP (FIG. 2) and that they are more sensitive to mitochondrial complex I inhibitor Phenformin (FIGS. 3A and 3B) and to L-asparaginase (glutamine/asparagine hydrolysis) (FIG. 3C). When Eµ-Myc-gapdh$^{high}$ cells were specifically silenced for gapdh (by 30%), they were more sensitive to phenformin (FIGS. 4A and 4B) and to L-asparaginase (FIG. 4C) treatment than control (shSCR) Eµ-Myc-gapdh$^{high}$ cells. In addition, B lymphoma progression is reduced upon phenformin treatment in Eµ-Myc-gapdh$^{low}$-bearing mice, as shown by the progression-free survival (FIG. 5A) and by the size of the axillary lymphomas (FIG. 5B) and the spleen (FIG. 5C).

From 'fresh' patient biopsies diagnosed as follicular lymphomas we could confirm that glycolytic tumors express more gapdh mRNA than Oxphos tumors.

Our collaborator Pr. Catherine Thieblemont performed a new clinical protocol targeting tumor mitochondrial metabolism (L-asparaginase+Torisel+Metformine+Rituximab) in which nine R-CHOP-refractory Myc+-DLBCL patients were included. Out of nine patients, three were in complete response (CR), one in partial response, one progressed on therapy and four were removed from the study because of treatment toxicity. Retrospectively, all three DLBCL in CR were expressing low level of GAPDH at diagnosis. One DLBCL expressing low level of GAPDH progressed on therapy.

REFERENCES

Throughout this application, various references describe the state of the art to which this invention pertains. The disclosures of these references are hereby incorporated by reference into the present disclosure.

Alizadeh, A. A., Eisen, M. B., Davis, R. E., Ma, C., Lossos, I. S., Rosenwald, A., Boldrick, J. C., Sabet, H., Tran, T., Yu, X., et al. (2000). Distinct types of diffuse large B-cell lymphoma identified by gene expression profiling. Nature 403, 503-511.

Monti S, Savage K J, Kutok J L, Feuerhake F, Kurtin P, Mihm M, Wu B, Pasqualucci L, Neuberg D, Aguiar R C, et al. Molecular profiling of diffuse large B-cell lymphoma identifies robust subtypes including one characterized by host inflammatory response. Blood. 2005; 105:1851-1861.

Miyoshi H. Structure-activity relationships of some complex I inhibitors. Biochimica et Biophysica Acta (BBA)—Bioenergetics 1998 Volume 1364 Issue 2 Pages 236-244.

Ramsay E E, Hogg P J, Dilda P J. Mitochondrial metabolism inhibitors for cancer therapy. Pharm Res. 2011 November; 28(11):2731-44.

Wise D R, Thompson C B. Glutamine Addiction: A New Therapeutic Target in Cancer Trends Biochem Sci. 2010 August; 35(8):427-33.

The invention claimed is:

1. A method for treating a lymphoma patient in need thereof with a mitochondrial metabolic inhibitor and/or a glutamine metabolism inhibitor, comprising:
    a) determining a level of glyceraldehyde-3-phosphate dehydrogenase (GAPDH) expression in lymphoma cells obtained from said patient,
    b) identifying the patient as a responder when the level of GAPDH expression is lower than a reference value obtained from healthy control subjects; and
    c) treating the patient identified in b) as a responder with a mitochondrial metabolic inhibitor and/or a glutamine metabolism inhibitor.

2. A method for treating a patient in need thereof with an immune checkpoint inhibitor, comprising:
    a) determining a level of glyceraldehyde-3-phosphate dehydrogenase (GAPDH) expression in lymphoma cells obtained from the patient, b) identifying the patient as a responder when the level of GAPDH expression is lower than a reference value obtained from healthy control subjects; and
    c) treating the patient identified in b) as a responder with an immune checkpoint inhibitor.

3. The method according to claim 1, wherein the patient is afflicted with a non-Hodgkin's B cell lymphoma.

4. The method according to claim 3, wherein the non-Hodgkin's B cell lymphoma is diffuse large B-cell lymphoma (DLBCL).

5. The method according to claim 1, wherein the mitochondrial metabolic inhibitor is a mitochondrial complex I inhibitor.

6. The method according to claim 5, wherein the mitochondrial complex I inhibitor is selected from the group consisting of biguanides, rotenoids, piericidins, capsaicins, pyridinium-type inhibitors and thiazolidinediones.

7. The method according to claim 5, wherein the mitochondrial complex I inhibitor is a biguanide selected from the group consisting of metformin, phenformin and buformin.

8. The method according to claim 1, wherein the glutamine metabolism inhibitor is L-asparaginase.

9. The method according to claim 2, wherein the immune checkpoint inhibitor is selected from the group consisting of an antibody, synthetic sequence peptides, native sequence peptides, small molecules which bind to immune checkpoint proteins and their ligands, and aptamers which bind to immune checkpoint proteins and their ligands.

* * * * *